United States Patent [19]

Munnerlyn

[11] Patent Number: 5,163,934

[45] Date of Patent: Nov. 17, 1992

[54] PHOTOREFRACTIVE KERATECTOMY

[75] Inventor: Charles R. Munnerlyn, Sunnyvale, Calif.

[73] Assignee: VISX, Incorporated, Sunnyvale, Calif.

[21] Appl. No.: 81,986

[22] Filed: Aug. 5, 1987

[51] Int. Cl.⁵ .......................... A61N 5/02; A61N 5/06
[52] U.S. Cl. .......................................... 606/5; 606/3; 606/10; 606/13; 128/395
[58] Field of Search ...................... 128/303.1, 362, 395; 219/121 L, 121 LA, 121 LH, 121 LP, 121 LQ, 121 LM; 606/2-5, 11-14

[56] References Cited

U.S. PATENT DOCUMENTS

| | | | |
|---|---|---|---|
| 3,330,182 | 7/1967 | Gerber et al. | 219/121.6 |
| 4,355,871 | 10/1982 | Nevyas et al. | 356/390 |
| 4,370,540 | 1/1983 | Davis et al. | 219/121 L |
| 4,648,400 | 3/1987 | Schneider et al. | 606/5 |
| 4,665,913 | 5/1987 | L'Esperance, Jr. | 606/5 |
| 4,724,522 | 2/1988 | Belgorod | 128/303.1 |
| 4,729,372 | 3/1988 | L'Esperance | 128/303.1 |
| 4,732,148 | 3/1988 | L'Esperance | 128/303.1 |
| 4,770,172 | 9/1988 | L'Esperance, Jr. | 128/395 |

OTHER PUBLICATIONS

"Advanced Techniques in Ophlthalmic Microsurgery" by Girard; The C. V. Mosby Company, St. Louis, Toronto, London; 1981 pp. 84, 107–110, 114, 116, 123.

Stephen L. Trokel, R. Srinivasan, and Bodil Braren, "Excimer Laser Surgery of the Cornea", American Journal of Ophthalmology, vol. 96, No. 6, Dec. 1983, pp. 710–715.

Marguerite B. McDonald and Herbert E. Kaufman, Chapter 21, pp. 431–432, "Epikeratophakia for Aphakia, Myopia, and Keratoconus in the Adult Patient", Refractive Corneal Surgery, published by Slack Incorporated, 6900 Grove Road, Thorofare, N.J. 08086.

Primary Examiner—David M. Shay
Attorney, Agent, or Firm—Oblon, Spivak, McClelland, Maier & Neustadt

[57] ABSTRACT

Photorefractive keratectomy is accomplished by an excimer laser beam that ablates away corneal tissue in a photo decomposition process. Before this occurs, the epithelium (21) of the cornea (20) is surgically removed to expose Bowman's layer (22) on the anterior surface of the stroma (23) and to begin the laser ablation at Bowman's layer. An excimer laser beam is preferred for this and is rotated during the ablation to average out energy density variations in the beam. The beam is also variably masked concentrically of its axis, during the ablation, to remove corneal tissue to varying depths as necessary for recontouring the anterior stroma. Afterward, epithelium (21) rapidly regrows and resurfaces the contoured area.

62 Claims, 4 Drawing Sheets

PHOTOREFRACTIVE KERATECTOMY

BACKGROUND

As discovered by Stephen L. Trokel ("Excimer Laser Surgery of the Cornea", *American Journal of Ophthalmology*, December 1983), far ultraviolet radiation from an excimer laser can be used to change the refractive power of the cornea of an eye. The radiation ablates away corneal tissue in a photo decomposition that does not cause thermal damage to adjacent tissue, and can be called photorefractive keratectomy. A similar photo decomposition of corneal tissue can achieved with an infrared laser operating near 2.9 micrometers, where thermal damage to adjacent tissue is minimized by the high absorption of water.

L'Esperance U.S. Pat. No. 4,665,913 describes procedures for changing the contour of the anterior surface of the cornea of the eye by directing pulses from an excimer laser in a scanning pattern that moves around the cornea. The laser pulses first ablate and remove the epithelium of the cornea, and then the ablation penetrates into the stroma of the cornea to change its contour for various purposes, such as correcting myopia or hyperopia. Schneider et al. U.S. Pat. No. 4,648,400 suggests radial keratectomy with an excimer laser that also ablates away the epithelium before penetrating into, and changing the contour of, the stroma of the cornea.

I have discovered inherent inaccuracies in the process of ablating corneal tissue with an excimer laser beam, and I have found ways of substantially improving the accuracy of the process. Understanding my invention, though, requires an understanding of the excimer laser beam and the structure of the cornea.

Excimer Laser Beam

Removing tissue from the cornea to establish a new profile for the cornea assumes that the energy density of the laser beam and the tissue removal rate are both accurately known. The tissue removal is not monitored and is accomplished merely by applying a predetermined quantity of radiant energy to the area being shaped. Unfortunately, the energy density of the excimer laser beam cannot be known with complete accuracy, and this makes its depth of penetration into tissue correspondingly uncertain. The output energy of the excimer laser is nonuniform in its energy distribution, and its beam diverges significantly more than most lasers.

A typical excimer laser, operating at 193 nm, has a beam profile that is 8 mm by 24 mm with a gaussian cross section to the short dimension and a ±10% uniformity over 80% of the long dimension. This beam profile is more suitable for forming a slit image than a uniform beam.

If the beam is made into a small area spot, as suggested L'Esperance in U.S. Pat. No. 4,665,913, then its energy density in different regions of the spot makes the bottom of each spot other than flat. This makes it impossible to form a smooth profile by accurately placing the spots adjacent to each other when the spots are not flat bottomed. The accurate placing of adjacent spots without overlap or gaps is also a formidable problem, even if the spots were flat bottomed. Beam variations also occur between pulses so that successive pulses can cause variable ablation depths, as well as produce different depths from gaps between spots or overlaps in spots.

Cornea Structure

The cornea is a thin shell with nearly concentric anterior and posterior surfaces and a central thickness of about 520 micrometers. It has an index of refraction of 1.377 and a nominal radius of curvature of 7.86 mm. The epithelium, forming the anterior surface of the cornea, is about 50 micrometers thick. The epithelial cells are capable of very rapid regrowth, and it is known that the epithelium can be removed from the cornea and will quickly regrow to resurface the area from which it was removed. Underlying the epithelium is a layer called Bowman's layer or Bowman's membrane, which is about 20 micrometers thick. This covers the anterior surface of the stroma, which makes up the bulk of the cornea and consists primarily of collagen fibers. The endothelium, forming the posterior layer of the cornea, is a single layer of cells that do not reproduce.

About three-quarters of the refractive power of the eye is determined by the curvature of the anterior surface of the cornea, so that changing the shape of the cornea offers a way to significantly reduce or eliminate a refractive error of the eye. Since the epithelium readily regrows, a change in the shape of the anterior surface of the cornea must be made by modifying Bowman's layer and the stroma to be permanent. The stroma is thick enough so that portions of its anterior region can be ablated away to change its profile and thus change the refractive power of the eye for corrective purposes, while leaving plenty of remaining stroma tissue. For example, a change of 5 diopters requires only 27 microns of stromal removal within a 4 mm diameter region.

SUMMARY OF THE INVENTION

I have devised ways of improving the accuracy of the laser ablation of corneal tissue so that the profile produced on the anterior surface of the cornea more accurately approximates what was intended. First, photo decomposition of corneal tissue by my method occurs only after surgically removing the epithelium so that the laser ablation is as shallow as possible. Since the energy density of the laser beam involves some inherent inaccuracy, and the total inaccuracy grows with the depth of the ablation, the shallowest possible ablation minimizes the inaccuracy of the profile being created on the cornea. This contrasts with the suggestions of Schneider et. al. U.S. Pat. No. 4,648,400 and L'Esperance U.S. Pat. No. 4,665,913, whose laser beams have to ablate through 50 microns of epithelium, with the inherent inaccuracies involved in penetrating to such a depth, before changing the cornea shape by ablating away stroma tissue.

Then, instead of scanning a small laser beam spot in a pattern that moves around the surface of the cornea, as suggested in L'Esperance U.S. Pat. No. 4,665,913, I size the laser beam to coincide with the entire area of interest of the cornea to be shaped. This eliminates the problems of gaps and overlaps between adjacent beam spots and allows each pulse of the laser beam to potentially cover the entire area of interest. To remove more tissue from selected regions of that area, I use variable masking that can concentrically reduce the area of the beam. A variable diameter aperture, an annulus with a variable inside diameter, and linear masks angularly orientable around the beam axis are three possibilities that I prefer for this.

I further improve the accuracy by rotating the laser beam, during the ablation, to average out beam density variations. Since excimer lasers are optimally operated to produce a pulsed output beam, I rotate the beam between pulses, so that random variations in beam density are averaged out to improve the uniformity of the beam density and the consequent uniformity of the ablation depth.

DRAWINGS

DETAILED DESCRIPTION

An instrument 10, for practicing photorefractive keratectomy according to my invention, preferably uses an excimer laser 11. Excimer lasers are generally known and available to emit a beam of ultraviolet radiation at 193 nm suitable for ablating away corneal tissue in a photo decomposition process that does not thermally damage adjacent tissue. My invention is not limited to any particular laser configuration, however, so that excimer laser 11 is shown schematically. Also, as previously mentioned, an infrared laser, operating near 2.9 micrometers, can be substituted for excimer laser 11. Whatever laser is used, its electromagnetic radiation should be at a wavelength that is highly absorbed by corneal tissue.

Presently, excimer laser beams differ from laser to laser, but each laser can be tuned to some extent to make its output beam more uniform in density. To determine the density variation in the output beam of a particular excimer laser, I direct the laser beam onto a smooth surface of a resin material such as polymethymethacrylate to ablate away the resin material and observe the uniformity of the ablation by producing interference fringes from the ablated surface. This information can then be used to fine tune the laser to improve the uniformity of the energy distribution in its output beam. Also, rotation of the laser beam relative to the resin surface has established that beam rotation averages out the energy distribution variations that are unavoidable in the laser beam and produces a more evenly ablated surface.

Figure 7:
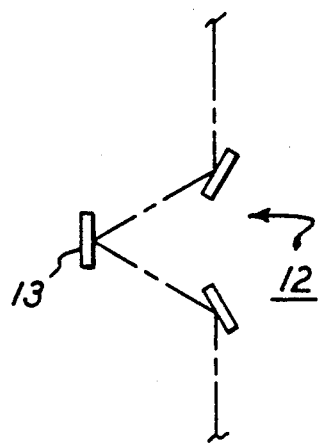
FIG. 7 is a partially schematic view of a K-mirror for rotating a laser beam to achieve the rotational effect shown in FIGS. 5 and 6.
Figure 8:
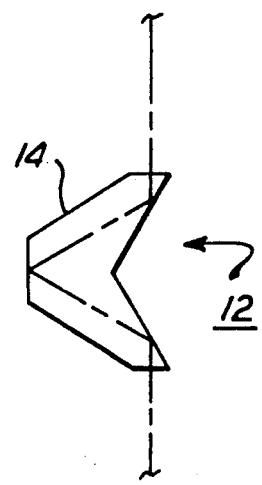
FIG. 8 is a partially schematic view of a dove prism for rotating a laser beam to achieve the rotational effect illustrated in FIGS. 5 and 6.

The beam rotator 12 for excimer laser 11 is preferably either K-mirror 13, as shown in FIG. 7, or dove prism 14, as shown in FIG. 8. In either case, the laser beam is reflected from its axis through three angles that direct it back to its axis, and the surfaces of mirrors or a prism accomplish the three reflections. These surfaces can be rotated in unison to rotate the beam on its axis; and since an excimer laser is preferably operated in a pulsed mode, I prefer that K-mirror 13 or dove prism 14 be rotated between each pulse so that successive pulses have different angular orientations. The beam can also be rotated at a constant rate selected to change the angular orientation of each succeeding pulse. These generally occur at a predetermined interval (a few pulses per second, for example) and have a short duration (20 nanoseconds, for example).

Figure 5:
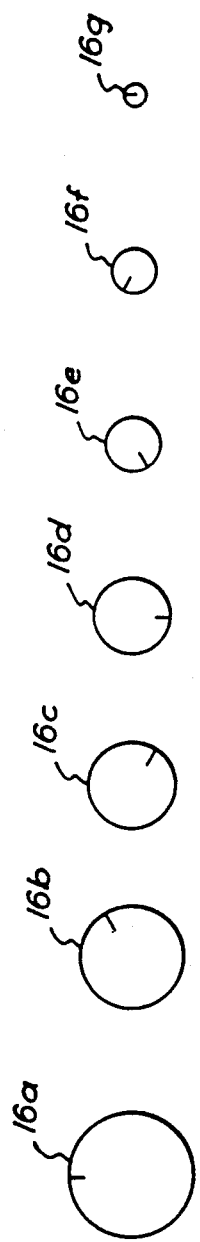
FIG. 5 is a partially schematic view of a succession of beam pulses that are rotated and diminished in area to accomplish the myopia correction of FIG. 3.

Mask 15 is disposed in the path of the laser beam to vary the beam size, concentrically of the beam axis. There are several ways that mask 15 can accomplish this. One way is a varying diameter aperture that can produce a succession of varying sized pulses 16a–g, as shown in FIG. 5. The schematic mark on pulses 16 shows beam rotation from pulse to pulse, and this can be in varying angular amounts. The rotation angle should be large enough so that the beam rotates through at least one revolution for the total number of pulses to be used.

Figure 6:
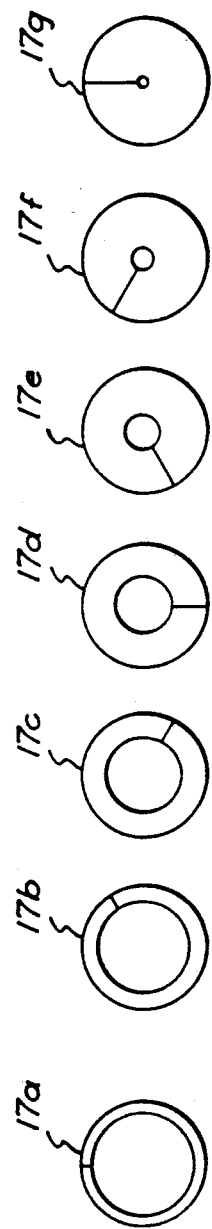
FIG. 6 is a partially schematic view of a succession of beam pulses that are rotated and varied in area to accomplish the hyperopia correction of FIG. 4.

Another preferred form of mask 15 is annuluses with varying inside diameters, producing the succession of beam pulses 17a–g, as shown in FIG. 6. Reticle masks applied with varying magnification, or variable diameter opaque regions centered on the axis of the beam, can accomplish the varying annuluses shown in pulses 17. These are also schematically marked for the preferred rotation of the laser beam between each pulse.

Figure 9:
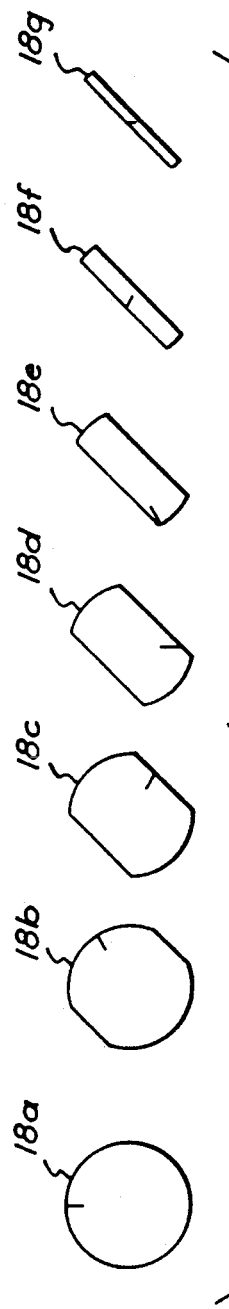
FIG. 9 is a partially schematic view of a succession of beam pulses that are rotated and varied in area for correcting astigmatism.

A mask suitable for correcting astigmatism is a variable width slit that can be positioned angularly of the optical axis of the eye to produce a succession of pulses 18 such as shown in FIG. 9. The long axis of variable width pulses 18 can be set at variable angular orientations, and the orientation selected for the pulses 18, of FIG. 9, is merely an example.

Figure 1:
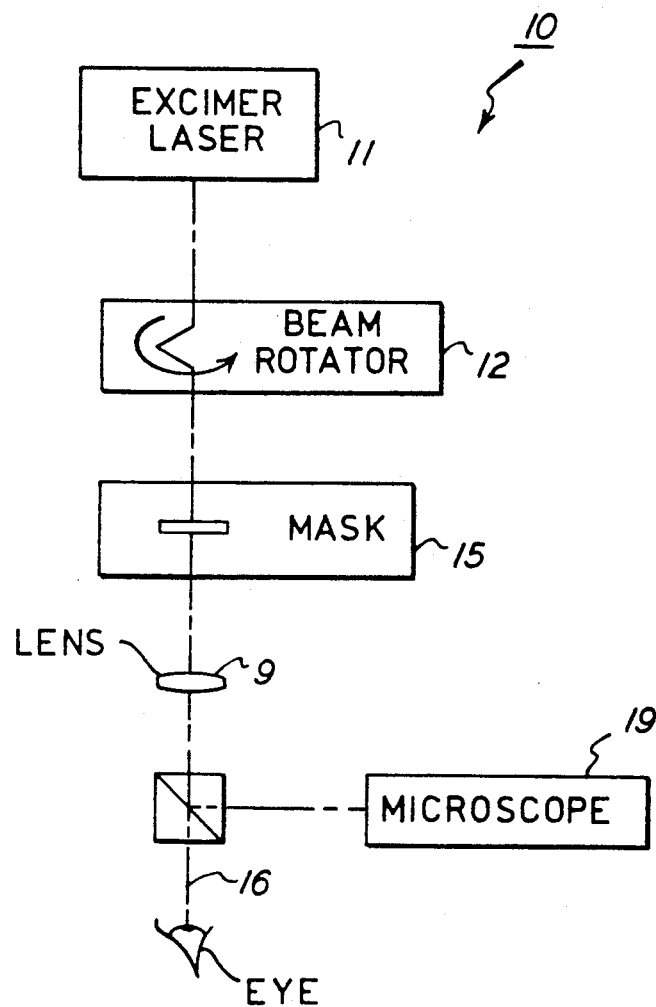
FIG. 1 is a schematic view of a preferred embodiment of an instrument for practicing photorefractive keratectomy according to my method.

Masks 15 for achieving the pulse patterns of FIGS. 5, 6, and 9 can be arranged either closely adjacent the eye, or spaced from the eye as shown in FIG. 1, where a lens 9 reimages mask 15 on the eye. Mask 15 can then include several mask reticle shapes in a turret that can index the mask reticles into the beam path where each reticle is reimaged by lens 9 onto the eye.

Instrument 10 also preferably includes a microscope 19 having a viewing path that coincides with the laser beam. Microscope 19 is useful for aligning the laser beam with the optical axis of the eye and for observing the photorefractive keratectomy as it proceeds.

Figure 2:
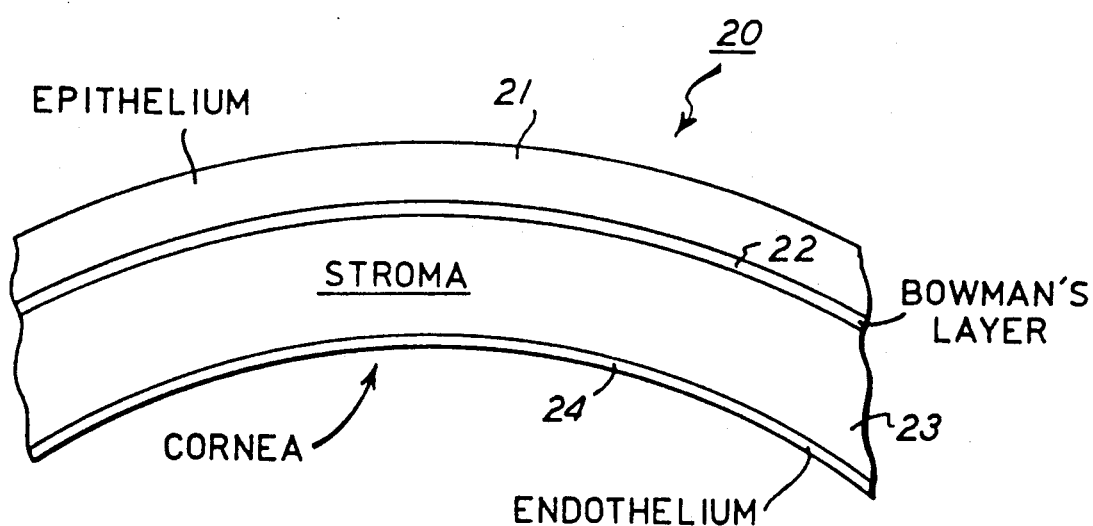
FIG. 2 is a fragmentary and partially schematic cross-sectional view of the cornea of an eye.

The known structure of a cornea 20 is shown in FIG. 2. This includes epithelium 21, forming the anterior surface of cornea 20, the epithelium being the smooth layer that regrows rapidly. Bowman's layer 22 is shown on the anterior surface of stroma 23. Bowman's layer 22 and the stroma 23 are layers that can accommodate permanent change in the contour of cornea 20. Endothelium 24, forming the posterior surface of the cornea, is a single cell layer that does not regrow.

Photo decomposition to ablate away corneal tissue occurs, according to my invention, only after epithelium 21 is surgically removed from the anterior surface of cornea 20. This can be done using absolute alcohol or a 4% cocaine solution on a blunted cellulose-tipped sponge followed by tissue removal with a Paton spatula, as described in Chapter 21 of *Refractive Corneal Surgery*, published by Slack, Incorporated, 6900 Groove Road, Thorofare, N.J., 08086. Chapter 21 is entitled "Epikeratophakia for Aphakia, Myopia, and Keratoconus in the Adult Patient", by Marguerite B. McDonald and Herbert E. Kaufman.

There may also be other ways of surgically removing epithelium 21. However, I prefer that epithelium 21 not be ablated away with a laser beam in a photo decomposition process, because of the inherent inaccuracies involved. Since different regions of an excimer laser beam differ in energy density, these beam regions ablate away tissue to varying depths. The unavoidable inaccuracies from this grow increasingly larger as the depth of the ablation increases. Ablating away 50 microns of epithelium 21 is subject to ablation depth inaccuracies of 5 microns (which is large enough for a significant refraction error), because of the uneven energy distribution characteristics of the laser beam. Thus, it is presently not possible to ablate away epithelium 21 with an excimer laser beam and accurately reach and stop exactly at Bowman's layer 22. Surgical removal of epithelium 21 can accomplish this, however; and this leaves only a shallow ablation cut for a laser beam to make on Bowman's layer 22 and the anterior of the stroma 23. Although inaccuracies from energy distribution in the laser beam also occur during ablation of the stroma 23, the total ablation depth inaccuracy can be minimized by making the ablation as shallow as possible. For a typical refractive correction, the total ablation depth can be reduced by a factor of 3 if the epithelium 21 is surgically removed first.

Figure 3:
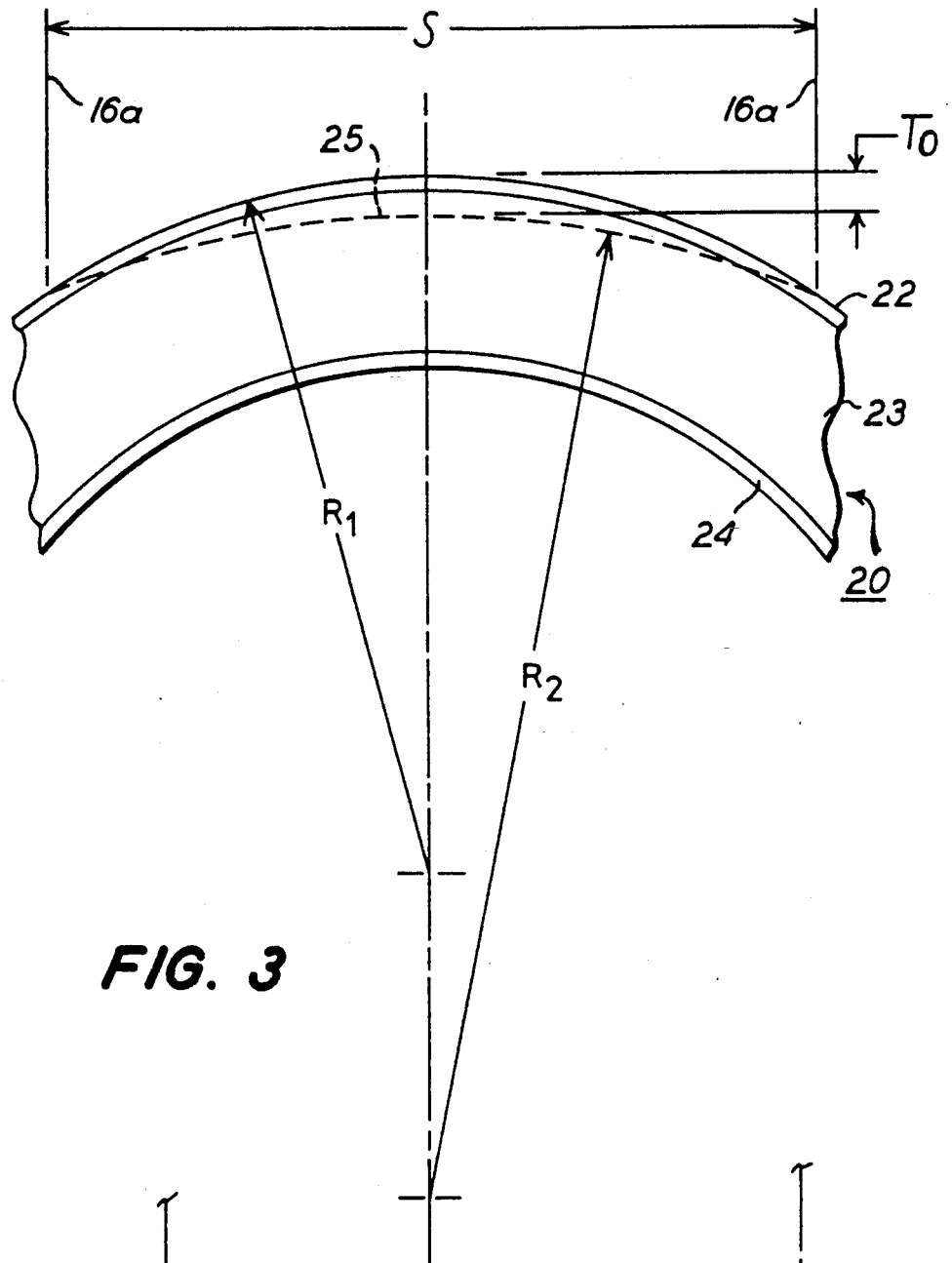
FIG. 3 is a fragmentary and partially schematic view of the cornea of FIG. 2 with the epithelium removed and showing a correction for myopia.

Ablation of the tissue of cornea 20, after removal of the epithelium 21, to correct for myopia is shown in FIG. 3. The laser beam 16 is adjusted to a circular spot 16a registered with the area of interest on cornea 20, this typically being a 3-10 mm circle. The correction for myopia reduces the radius of curvature of cornea 20 to the contour of broken line 25. This requires removal of more tissue in the center of cornea 20 and less tissue toward the peripheral area of beam spot 16a. A first pulse 16a can ablate away tissue from the entire area of interest, but successive pulses 16b-g are reduced in diameter by mask 15 (and also rotated on the beam axis by beam rotator 12) so that the pulses become successively smaller. This removes more tissue from the central region and brings the cornea to the desired contour having the longer radius of broken line 25. After the photorefractive keratectomy, epithelium 21 rapidly regrows over the shaped area, producing a new anterior surface of the cornea 20.

The mathematics of the photorefractive keratectomy to correct for myopia, as shown in FIG. 3, involve lengthening the radius of curvature of the anterior stroma from its original radius $R_1$ to the new radius $R_2$ of broken line 25. This occurs in a circular area having a diameter S and requires tissue removal to a maximum depth of $t_O$, on the optical axis of cornea 20. The correction expressed in diopters is given by:

$$D = (n-1)(1/R_2 - 1/R_1)$$

where n = 1.377 (the index of refraction of cornea 20). From the geometry of FIG. 3, the thickness of removed corneal tissue can be approximated by:

$$t_O \delta = S^2 D/8 (n-1)$$

This shows that the maximum depth of tissue removal $t_O$ is approximately 3 microns per diopter for an optical zone 16a that is 3 mm in diameter. For a 4 mm diameter optical zone 16a, the depth of the removed tissue increases to 5.3 microns per diopter; and for a 5 mm diameter optical zone 16a, the tissue removal depth increases to 8.3 microns per diopter. Tissue can be ablated to these relatively shallow depths with significantly greater accuracy than if the ablation depth is increased by the 50 micrometer thickness of the epithelium.

Figure 4:
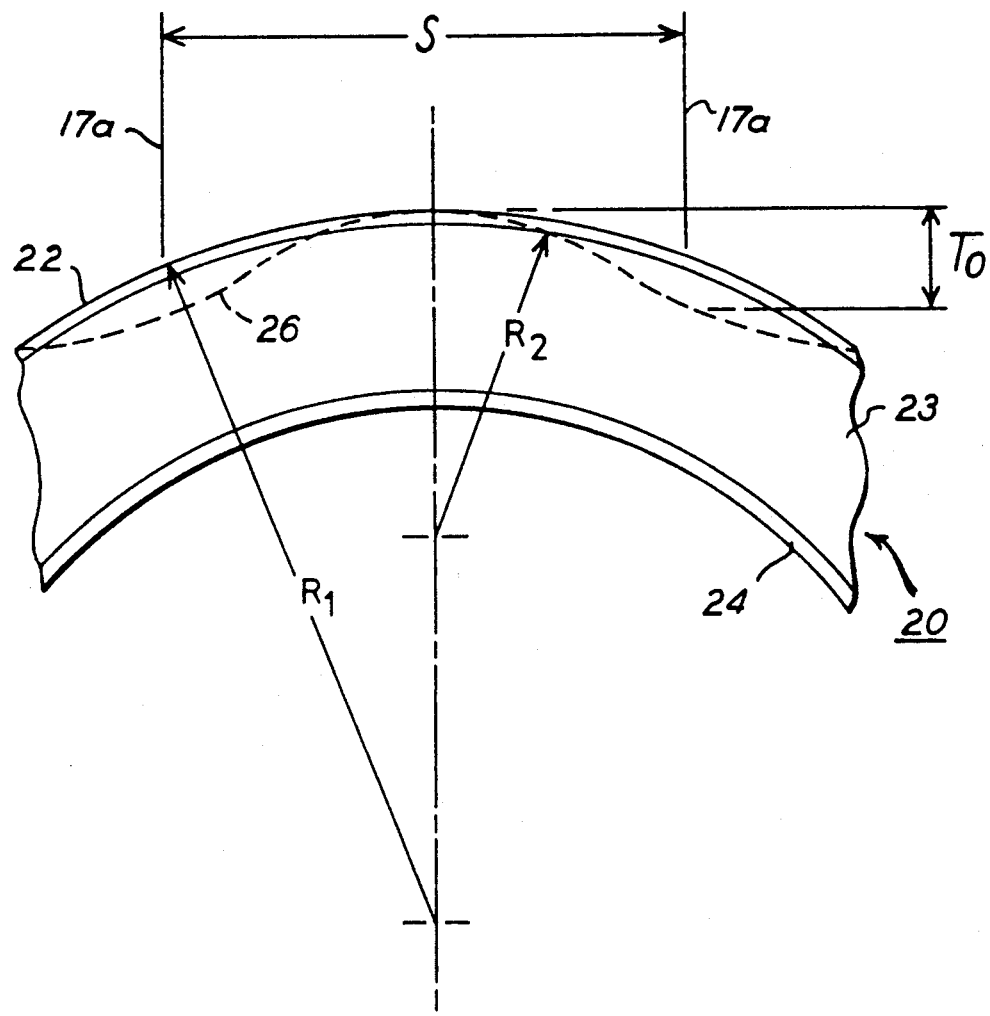
FIG. 4 is a fragmentary and partially schematic cross-sectional view of the cornea of FIG. 2 with the epithelium removed and showing a correction for hyperopia.

For correcting hyperopia, as shown in FIG. 4, beam 17a covers the entire area of interest of cornea 20, but more tissue must be removed from the periphery of the area of interest, than from the center of the area, so that the radius of curvature can be increased from the original radius $R_1$ to the new radius $R_2$ of broken line 26. This is done by masking beam 17a to an annular shape with a varying inside diameter (and rotating the beam between successive pulses 17a-g) as shown in FIG. 6. The first pulse 17a ablates away only peripheral tissue, and each succeeding pulse 17b-g ablates away tissue for a greater distance inward from the peripheral region. The outer diameter of the mask can be slowly increased during the ablation so that the ablation depth tapers at the outer periphery. Within this, the successive pulses 17a-g of gradual thickening shape contour cornea 20 to the shorter radius of curvature $R_2$ of surface 26. Again, after cornea 20 is contoured, its epithelium 21 regrows to produce a new anterior surface. The maximum depth of tissue removal $t_O$, in an annular region around the optical cornea 20, is about 3 microns per diopter for a 3 mm diameter region 17a. This increases to 5.3 microns per diopter for a 4 mm diameter optical zone 17a, and to 8.3 microns per diopter for a 5 mm diameter optical zone 17a.

Each pulse from excimer laser 11 can ablate away 0.3 to 0.6 microns of corneal tissue so that several pulses are necessary for each micron of penetration into stroma tissue. A typical correction, involving several microns of penetration, thus requires a large enough number of pulses so that the pulses can be rotated through several revolutions in a pulse sequence to average out beam density variations.

Experimental results have verified that photorefractive keratectomy according to my invention can be made substantially more accurate. Surgical removal of epithelium 21 contributes to the accuracy attainable, by keeping the ablation depth as shallow as possible to minimize the inherent inaccuracy in varying energy densities of the beam. Using a beam with its axis fixed in the center of the area to be shaped and rotating the beam around its axis increases accuracy by averaging out the beam density variations. This also avoids the formidable problems of gaps and overlaps inherent in scanning a small spot in a pattern around the area to be contoured. Keeping the beam axis fixed requires masking the beam to ablate tissue to varying depths in the area being shaped, but this is readily done with masks concentric with the beam axis. Photorefractive keratectomy, according to my invention, is not limited to the myopia and hyperopia corrections illustrated and can be used for contouring cornea tissue for any feasible purpose.

I claim:

1. A photorefractive keratectomy method for operating on an eye having a cornea, said cornea having an anterior surface and comprising an epithelium, a Bowman's layer, and stroma, said epithelium, said Bowman's layer, and said stroma each having an anterior surface, said method comprising the steps of:
   (a) mechanically removing said epithelium from the anterior surface of said cornea to clear said epithelium away from a selected region of said cornea and to expose the anterior surface of said Bowman's layer in said selected region; and
   (b) after exposing said Bowman's layer, directing a beam of electromagnetic radiation in a wavelength highly absorbed by corneal tissue onto an area of said Bowman's layer in said selected region of said cornea to accomplish ablative photo decomposition to a depth in said selected region, beginning with said Bowman's layer and penetrating into the anterior stroma of said cornea.

2. The method of claim 1 including using a series of pulses of said radiation and rotating said beam around an axis of said beam to different angular orientations for successive ones of said pulses.

3. The method of claim 1 including using a series of pulses of said radiation and variably masking successive pulses so that said pulses of said beam vary in size and are incident on various concentrically overlapping portions of said selected region.

4. The method of claim 3 including using a variable diameter aperture for varying the diameters of said successive pulses.

5. The method of claim 3 including using an annular mask having a variable diameter opaque central region.

6. The method of claim 3 including rotating said beam around an axis of said beam to different angular orientations for successive ones of said pulses.

7. The method of claim 1 wherein:
   (a) the area exposed to electromagnetic radiation has a periphery, a center, and an outer dimension;
   (b) more tissue is removed from the periphery than from the center of the area exposed to electromagnetic radiation; and
   (c) the outer dimension of the area exposed to electromagnetic radiation is slowly increased during the ablative photo decomposition so that the depth tapers at the periphery of the area exposed to electromagnetic radiation.

8. The method of claim 7 wherein the outer periphery of the area exposed to electromagnetic radiation is circular.

9. A method of using an instrument that produces a pulsed beam of electromagnetic radiation in a wavelength highly absorbed by corneal tissue for performing a photorefractive keratectomy on an eye having a cornea, said cornea having an anterior surface and comprising an epithelium, a Bowman's layer, and stroma, said epithelium, said Bowman's layer, and said stroma each having an anterior surface, said method comprising the steps of:
   (a) preparing a selected region of said cornea for ablative photo decomposition produced by said beam by mechanically removing said epithelium from the anterior surface of said selected region of said cornea to clear said epithelium away from said selected region and to expose the anterior surface of said Bowman's layer in said selected region; and
   (b) after removing said epithelium and exposing the anterior surface of said Bowman's layer in said selected region, then directing pulses of said beam onto an area of said Bowman's layer in said selected region to accomplish said ablative photo decomposition of corneal tissue in said selected region to a depth, so that said pulses of said beam ablatively photo decompose stromal tissue.

10. The method of claim 9 including rotating said beam around an axis of said beam to change the angular orientation of said beam in successive pulses of said beam.

11. The method of claim 10 including using a K-mirror for rotating said beam.

12. The method of claim 10 including using a dove prism for rotating said beam.

13. The method of claim 9 including variably masking successive pulses of said beam concentrically of said beam so that said pulses differ in area and cover various overlapping concentric portions of a selected region of said cornea centered on said beam axis.

14. The method of claim 13 including using a variable diameter aperture for masking said beam.

15. The method of claim 13 including using an annular mask having a variable inside diameter for masking said beam.

16. The method of claim 9 wherein:
   (a) the area exposed to electromagnetic radiation has a periphery, a center, and an outer dimension;
   (b) more tissue is removed from the periphery than from the center of the area exposed to electromagnetic radiation; and
   (c) the outer dimension of the area exposed to electromagnetic radiation is slowly increased during the ablative photo decomposition so that the depth tapers at the periphery of the area exposed to electromagnetic radiation.

17. The method of claim 16 wherein the outer periphery of the area exposed to electromagnetic radiation is circular.

18. A photorefractive keratectomy method for operating on an eye having a cornea, said cornea having an anterior surface and comprising an epithelium, a Bowman's layer, and stroma, said epithelium, said Bowman's layer, and said stroma each having an anterior surface, said method comprising the steps of:
   (a) mechanically removing said epithelium from the anterior surface of said cornea to clear said epithelium away from a selected region of said cornea to expose the anterior surface of said Bowman's layer in said selection region;
   (b) forming a beam of electromagnetic radiation in a wavelength highly absorbed by corneal tissue and directing said radiation beam onto an area of said selected region of said Bowman's layer after exposing said Bowman's layer in said selected region for ablatively photo decomposing said selected region of said cornea to a depth;
   (c) while keeping an axis of said beam centered within said selected region, variably masking said beam concentrically of said axis for varying the area of said beam to vary the ablatively photo decomposed profile of said selected region of said cornea; and
   (d) rotating said beam around said axis to change the angular orientation of said beam during the photo decomposition.

19. The method of claim 18 including using a variable diameter aperture for variably masking said beam.

20. The method of claim 18 including using an annular mask having a variable inside diameter for variably masking said beam.

21. The method of claim 18 including pulsing said beam, and applying said variable masking and said rotating of said beam to successive pulses of said beam.

22. The method of claim 18 wherein:
(a) the area exposed to electromagnetic radiation has a periphery, a center, and an outer dimension;
(b) more tissue is removed from the periphery than from the center of the area exposed to electromagnetic radiation; and
(c) the outer dimension of the area exposed to electromagnetic radiation is slowly increased while ablatively photo decomposing said selected region of said cornea so that the depth tapers at the periphery of the area exposed to electromagnetic radiation.

23. The method of claim 22 wherein the outer periphery of the area exposed to electromagnetic radiation is circular.

24. The method of changing optical properties of an eye by operating solely upon the optically used area of the anterior surface of the cornea of an eye, which comprises the preliminary step of removing only the epithelial layer from said area, whereby within said area the cornea is epithelium-free, and then within said area subjecting the cornea to selective tissue-ablating laser radiation to selectively ablate the anterior surface of the cornea in a volumetric removal of corneal tissue and with depth penetration into the stroma to achieve a predetermined corneal profile.

25. The method of claim 24 including using a series of pulses of said laser radiation and rotating the beam of laser radiation to different angular orientation for successive ones of said pulses.

26. The method of claim 24 wherein:
(a) more tissue is removed from the periphery than from the center of the area exposed to laser radiation and
(b) the outer dimension of the area exposed to laser radiation is slowly increased during the ablation so that the ablation depth tapers at the outer periphery of the area exposed to laser radiation.

27. The method of claim 26 wherein the outer periphery of the area exposed to laser radiation is circular.

28. The method of claim 24 including using a series of pulses of said laser radiation and variably masking successive pulses so that said pulses of said laser radiation vary in size and are incident on various overlapping portions of said area.

29. The method of claim 28 including using a variable diameter aperture for varying the diameter of said successive pulses.

30. The method claim 28 including using an annular mask having a variable diameter opaque central region.

31. The method of claim 28 including rotating said laser radiation around an axis to different angular orientation for successive ones of said pulses.

32. The method of changing the anterior surface of the cornea of an eye from an initial curvature in an optically used area having defective optical properties to a subsequent curvature having correctively improved optical properties within said optically used area, which method comprises the preliminary step of removing only the epithelial layer from said area, whereby within said area Bowman's membrane is the externally exposed anterior surface of the cornea, and then directionally and within said area impacting said externally exposed surface with tissue-ablating laser radiation to selectively ablate the anterior surface of the cornea with penetration into the stroma and within volumetric sculpturing removal of corneal tissue to such penetration depth and profile as to characterize the anterior surface of the cornea with said subsequent curvature.

33. The method of claim 32 including using a series of pulses of said laser radiation and rotating the beam of laser radiation to different angular orientation for successive ones of said pulses.

34. The method of claim 32 wherein:
(a) the area exposed to laser radiation has a periphery, a center, and an outer dimension;
(b) more tissue is removed from the periphery than from the center of the area exposed to laser radiation; and
(c) the outer dimension of the area exposed to laser radiation is slowly increased during the ablation so that the ablation depth tapers at the periphery of the area exposed to laser radiation.

35. The method of claim 34 wherein the outer periphery of the area exposed to laser radiation is circular.

36. The method of claim 32 including using a series of pulses of said laser radiation and variably masking successive pulses so that said pulses of said laser radiation vary in size and are incident on various overlapping portions of said area.

37. The method of claim 36 including rotating said laser radiation around an axis to different angular orientation for successive ones of said pulses.

38. The method of claim 36 including using an annular mask having a variable diameter opaque central region.

39. The method of claim 36 including using a variable diameter aperture for varying the diameter of said successive pulses.

40. The method of changing optical properties of an eye by operating solely upon the optically used area of the anterior surface of the cornea of an eye, which comprises the preliminary step of removing only the epithelial layer from said area, whereby within said area the cornea is epithelium-free, and then within said area subjecting the cornea to selective ultraviolet radiation and attendant ablative photodecomposition in a volumetric removal of corneal tissue and with depth penetration into the stroma to achieve a predetermined corneal profile.

41. The method of claim 40 including using a series of pulses of said laser radiation and rotating the beam of laser radiation to different angular orientation for successive ones of said pulses.

42. The method of claim 40 wherein:
(a) the area exposed to ultraviolet radiation has a periphery, a center, and an outer dimension;
(b) more tissue is removed from the periphery than from the center of the area exposed to ultraviolet radiation and
(c) the outer dimension of the area exposed to ultraviolet radiation is slowly increased during the ablation so that the ablation depth tapers at the periphery of the area exposed to ultraviolet radiation.

43. The method of claim 42 wherein the outer periphery of the area exposed to laser radiation is circular.

44. The method of claim 40 including using a series of pulses of said laser radiation and variably masking successive pulses so that said pulses of said laser radiation vary in size and are incident on various overlapping portions of said area.

45. The method of claim 44 including rotating said laser radiation around an axis to different angular orientation for successive ones of said pulses.

46. The method claim 44 including using an annular mask having a variable diameter opaque central region.

47. The method of claim 44:
(a) wherein the selective tissue-ablating laser radiation is provided in the form of a beam having a diameter and
(b) including using a variable diameter aperture for varying the diameter of the beam.

48. The method of changing the anterior surface of the cornea of an eye having a cornea, said cornea having an anterior surface and an optically used area and comprising an epithelium, a Bowman's layer, and stroma, said epithelium, said Bowman's layer, and said stroma each having an anterior surface, said method changing the anterior surface of said cornea from an initial curvature in said optically used area having defective optical properties to a depth and a subsequent curvature having correctively improved optical properties within said optically used area, which method comprises the preliminary step of removing only said epithelium from said area, whereby within said area Bowman's layer is the externally exposed anterior surface of said cornea, and then directionally and within said area impacting said externally exposed surface with ultraviolet radiation to selectively ablate the anterior surface of said cornea by photo decomposition with penetration into said stroma and with volumetric sculpturing removal of corneal tissue to such penetration depth and profile as to characterize the anterior surface of said cornea with said subsequent curvature.

49. The method of claim 48 including using a series of pulses of said laser radiation and rotating the beam of laser radiation to different angular orientation for successive ones of said pulses.

50. The method of claim 48 including using a series of pulses of said laser radiation and variably masking successive pulses so that said pulses of said laser radiation vary in size and are incident on various overlapping portions of said area.

51. The method of claim 50:
(a) wherein the selective tissue-ablating laser radiation is provided in the form of a beam having a diameter and
(b) including using a variable diameter aperture for varying the diameter of the beam.

52. The method claim 50 including using an annular mask having a variable diameter opaque central region.

53. The method of claim 48 wherein:
(a) the area exposed to ultraviolet radiation has a periphery, a center, and an outer dimension;
(b) more tissue is removed from the periphery than from the center of the area exposed to ultraviolet radiation; and
(c) the outer dimension of the area exposed to ultraviolet radiation is slowly increased during the photo decomposition so that the depth tapers at the periphery of the area exposed to ultraviolet radiation.

54. The method of claim 53 wherein the outer periphery of the area exposed to laser radiation is circular.

55. The method of claim 53 including rotating said laser radiation around an axis to different angular orientation for successive ones of said pulses.

56. The method of claim 48 or claim 40, or claim 32 or claim 24 in which the radiation exposure is such as to develop anterior-surface curvature correction with depth penetration of several microns.

57. The method of claim 48 or claim 40 or claim 32 or claim 24 in which epithelial-layer removal is via gentle mechanical scraping.

58. The method of claim 48 or claim 40, or claim 32 or claim 24 in which the area of radiation is circular.

59. The method of changing the optical properties of an eye by operating solely upon the optically used area of the anterior surface of the cornea of an eye, which comprises the preliminary step of mechanically removing only the epithelial layer from said area, whereby within said area the cornea is epithelium-free, and then within said area subjecting the cornea to selective tissue-ablating laser radiation to selectively ablate the exposed surface of the cornea in a volumetric removal of corneal tissue and with depth penetration into the cornea.

60. The method of changing the optical properties of an eye by operating solely upon the optically used area of the anterior surface of an eye which comprises:
(a) the preliminary step of mechanically removing only the epithelial layer from said area, whereby within said area the cornea is epithelium-free, and then
(b) within said area subjecting the cornea to selective tissue-ablating laser radiation to selectively ablate the exposed surface of the cornea in a volumetric removal of corneal tissue and with depth penetration into the cornea to achieve a predetermined stroma profile.

61. The method of improving optical properties of an eye by operating essentially only upon the optically used area of the anterior surface of the cornea of the eye, which method comprises a one-step procedure of tissue-ablating laser radiation of the anterior surface of the cornea in a volumetric removal of corneal tissue to a predetermined curvature profile after the epithelium has been mechanically removed, said step being one of selectively distributing the tissue-ablating radiation to exposed corneal tissue within said area to achieve the predetermined curvature profile essentially only by volumetric removal of corneal tissue, and terminating said procedure upon achieving the predetermined curvature profile.

62. The method of changing the anterior surface of the cornea of an eye from an initial curvature in an optically used area having defective optical properties to a subsequent curvature having correctively improved properties within said optically used area, which method comprises:
(a) mechanically removing only the epithelial layer from said area, whereby within said area Bowman's membrane is the externally exposed anterior surface of the cornea; and
(b) then directionally within said area impacting said exposed surface with tissue-ablating laser radiation to ablate the exposed surface of the cornea with volumetric removal of corneal tissue to such penetration depth and profile as to characterize the anterior surface of the cornea with said subsequent curvature.

* * * * *

UNITED STATES PATENT AND TRADEMARK OFFICE
CERTIFICATE OF CORRECTION

PATENT NO. : 5,163,934

DATED : November 17, 1992

INVENTOR(S) : Charles R. Munnerlyn

It is certified that error appears in the above-indentified patent and that said Letters Patent is hereby corrected as shown below:

Column 1, line 14, after "can" insert --be--;
  line 60, change "L'Esperance in" to --in L'Esperance--.

Column 6, delete line 2 in its entirety and insert:
$$t_o \simeq -S^2 D/8(n-1)$$

Column 7, lines 48-50, delete in their entirety and insert therefor
  --8. The method of claim 7 wherein:
    (a) the area exposed to electromagnetic radiation has an outer periphery and
    (b) the outer periphery of the area exposed to electromagnetic radiation is circular.--.

Column 8, lines 37-39, delete in their entirety and insert therefor
  --17. The method of claim 16 wherein:
    (a) the area exposed to electromagnetic radiation has an outer periphery and
    (b) the outer periphery of the area exposed to electromagnetic radiation is circular.--.

Column 9, lines 19-46, delete in their entirety and insert therefor

UNITED STATES PATENT AND TRADEMARK OFFICE
CERTIFICATE OF CORRECTION

PATENT NO. : 5,163,934

DATED : November 17, 1992

INVENTOR(S) : Charles R. Munnerlyn

It is certified that error appears in the above-indentified patent and that said Letters Patent is hereby corrected as shown below:

--23. The method of claim 22 wherein:
(a) the area exposed to electromagnetic radiation has an outer periphery and
(b) the outer periphery of the area exposed to electromagnetic radiation is circular.

24. The method of changing optical properties of an eye having a cornea, said cornea having an anterior surface and an optically used area and comprising an epithelium, a Bowman's layer, and stroma, said epithelium, said Bowman's layer, and said stroma each having an anterior surface, said method being effected by operating solely upon said area, which comprises the preliminary step of removing only said epithelium from said area, whereby within said area said cornea is epithelium-free, and then within said area subjecting said cornea to selective tissue-ablating laser radiation to selectively ablate the anterior surface of said cornea in a volumetric removal of corneal tissue and with depth penetration into said stroma to achieve a predetermined corneal profile.

25. The method of claim 24:
(a) wherein the selective tissue-ablating laser radiation is provided in the form of a beam and
(b) including using a series of pulses of said laser radiation and rotating the beam of laser radiation to different angular orientations for successive ones of said pulses.

26. The method of claim 24 wherein:
(a) the area exposed to laser radiation has a periphery, a center, and an outer dimension;
(b) more tissue is removed from the periphery than from the center of the area exposed to laser radiation, and
(c) the outer dimension of the area exposed to laser radiation is slowly increased during the ablation so that

UNITED STATES PATENT AND TRADEMARK OFFICE
CERTIFICATE OF CORRECTION

PATENT NO. : 5,163,934

DATED : November 17, 1992

INVENTOR(S) : Charles R. Munnerlyn

It is certified that error appears in the above-indentified patent and that said Letters Patent is hereby corrected as shown below:

the ablation depth tapers at the outer periphery of the area exposed to laser radiation.
    27. The method of claim 26 wherein:
    (a) the area exposed to laser radiation has an outer periphery and
    (b) the outer periphery of the area exposed to laser radiation is circular.--;
    lines 52-54, delete in their entirety and insert therefor
    --29. The method of claim 28:
    (a) wherein each successive pulse has a diameter and
    (b) including using a variable diameter aperture for varying the diameter of said successive pulses.--;
    lines 60-68, delete in their entirety and insert therefor
    --32. The method of changing the anterior surface of the cornea of an eye having a cornea, said cornea having an anterior surface and an optically used area and comprising an epithelium, a Bowman's layer, and stroma, said epithelium, said Bowman's layer, and said stroma each having an anterior surface, said method changing the anterior surface of said cornea from an initial curvature in said optically used area having defective optical properties to a subsequent curvature having correctively improved optical properties within said optically used area, which method comprises the preliminary step of removing only said epithelium from said area, whereby within said area said Bowman's layer is the externally exposed anterior surface of said cornea, and then directionally and within said area impacting said externally exposed surface with tissue-ablating laser radiation to selectively ablate the anterior surface of said cornea with penetration into said stroma and with volumetric sculpturing removal of corneal tissue to

UNITED STATES PATENT AND TRADEMARK OFFICE
CERTIFICATE OF CORRECTION

PATENT NO. : 5,163,934

DATED : November 17, 1992

INVENTOR(S) : Charles R. Munnerlyn

It is certified that error appears in the above-indentified patent and that said Letters Patent is hereby corrected as shown below:

such penetration depth and profile as to characterize the anterior surface of said cornea with said subsequent curvature.--.

Column 10, lines 1-8, delete in their entirety;
    lines 9-12, delete in their entirety and insert therefor
        --33. The method of claim 32:
        (a) wherein the selective tissue-ablating laser radiation is provided in the form of a beam and
        (b) including using a series of pulses of said laser radiation and rotating the beam of laser radiation to different angular orientations for successive ones of said pulses.--;
    lines 23 and 24, delete in their entirety and insert therefor
        --35. The method of claim 34 wherein:
        (a) the area exposed to laser radiation has an outer periphery and
        (b) the outer periphery of the area exposed to laser radiation is circular.--
    lines 36-53, delete in their entirety and insert therefor
        --39. The method of claim 36:
        (a) wherein the selective tissue-ablating laser radiation is provided in the form of a beam and
        (b) including using a variable diameter aperture for varying the diameter of said successive pulses.
        40. The method of changing optical properties of an eye having a cornea, said cornea having an anterior surface and an optically used area and comprising an epithelium, a Bowman's layer, and stroma, said epithelium, said Bowman's layer, and said stroma each having an anterior surface, said

UNITED STATES PATENT AND TRADEMARK OFFICE
CERTIFICATE OF CORRECTION

PATENT NO. : 5,163,934                    Page 5 of 8

DATED : November 17, 1992

INVENTOR(S) : Charles R. Munnerlyn

It is certified that error appears in the above-indentified patent and that said Letters Patent is hereby corrected as shown below:

method changing the optical properties of the eye by operating solely upon the optically used area of the anterior surface of said cornea, which comprises the preliminary step of removing only said epithelium from said area, whereby within said area said cornea is epithelium-free, and then within said area subjecting said cornea to selective ultraviolet radiation and attendant ablative photo decomposition in a volumetric removal of corneal tissue and with depth penetration into said stroma to achieve a predetermined corneal profile.

41. The method of claim 40:
    (a) wherein the selective tissue-ablating layer radiation is provided in the form of a beam and
    (b) including using a series of pulses of said laser radiation and rotating the beam of laser radiation to different angular orientations for successive ones of said pulses.--;

lines 64 and 65, delete in their entirety and insert therefor

--43. The method of claim 42 wherein:
    (a) the area exposed to ultraviolet radiation has an outer periphery and
    (b) the outer periphery of the area exposed to ultraviolet radiation is circular.--.

Column 11, lines 18 and 19, after "epithelium" delete ".";
    lines 38-41, delete in their entirety and insert therefor --49. The method of claim 48:
    (a) wherein the selective tissue-ablating laser radiation is provided in the form of a beam and
    (b) including using a series of pulses of said laser radiation and rotating the beam of laser radiation to

UNITED STATES PATENT AND TRADEMARK OFFICE
CERTIFICATE OF CORRECTION

PATENT NO. : 5,163,934

DATED : November 17, 1992

INVENTOR(S) : Charles R. Munnerlyn

It is certified that error appears in the above-indentified patent and that said Letters Patent is hereby corrected as shown below:

different angular orientations for successive ones of said pulses.--.

Column 12, lines 13-67, delete in their entirety and insert therefor

--59. The method of changing the optical properties of an eye having a cornea that is circular in shape, said cornea having an anterior surface and an optically used area and comprising an epithelium, a Bowman's layer, and stroma, said epithelium, said Bowman's layer, and said stroma each having an anterior surface, the method changing the optical properties of the eye by operating solely upon said optically used area of the anterior surface of said cornea, which comprises the preliminary step of mechanically removing only said epithelium from said area, whereby within said area said cornea is epithelium-free and has an exposed surface, and then within said area subjecting said cornea to selective tissue-ablating laser radiation to selectively ablate said exposed surface of said cornea in a volumetric removal of corneal tissue and with depth penetration into said cornea.

60. The method of changing the optical properties of an eye having a cornea, said cornea having an anterior surface and an optically used area and comprising an epithelium, a Bowman's layer, and stroma, said epithelium, said Bowman's layer, and said stroma each having an anterior surface, the method changing the optical properties of the eye by operating solely upon said optically used area of the anterior surface of said cornea, said method comprising the steps of:

(a) the preliminary step of mechanically removing only said epithelium from said area, whereby within said area said cornea is epithelium-free and has an exposed surface,

UNITED STATES PATENT AND TRADEMARK OFFICE
CERTIFICATE OF CORRECTION

PATENT NO. : 5,163,934

DATED : November 17, 1992

INVENTOR(S) : Charles R. Munnerlyn

It is certified that error appears in the above-indentified patent and that said Letters Patent is hereby corrected as shown below:

and then
    (b) within said area subjecting said cornea to selective tissue-ablating laser radiation to selectively ablate said exposed surface of said cornea in a volumetric removal of corneal tissue and with depth penetration into said cornea to achieve a predetermined stroma profile.

61. The method of improving optical properties of an eye having a cornea, said cornea having an anterior surface and an optically used area and comprising an epithelium, a Bowman's layer, and stroma, said epithelium, said Bowman's layer, and said stroma each having an anterior surface, the method improving the optical properties of the eye by operating essentially only upon said optically used area of the anterior surface of said cornea, which method comprises a one-step procedure of tissue-ablating laser radiation of the anterior surface of said cornea in a volumetric removal of corneal tissue to a predetermined curvature profile after said epithelium has been mechanically removed, said step being one of selectively distributing the tissue-ablating radiation to exposed corneal tissue within said area to achieve said predetermined curvature profile essentially only by volumetric removal of corneal tissue, and terminating said procedure upon achieving said predetermined curvature profile.

62. The method of changing the anterior surface of the cornea of an eye having a cornea, said cornea having an anterior surface and an optically used area and comprising an epithelium, a Bowman's layer, and stroma, said epithelium, said Bowman's layer, and said stroma each having an anterior surface, the method changing the anterior surface of said cornea from an initial curvature in said optically used area having defective optical properties to a subsequent curvature having correctively improved optical

UNITED STATES PATENT AND TRADEMARK OFFICE
CERTIFICATE OF CORRECTION

PATENT NO. : 5,163,934

DATED : November 17, 1992

INVENTOR(S) : Charles R. Munnerlyn

It is certified that error appears in the above-indentified patent and that said Letters Patent is hereby corrected as shown below:

properties within said optically used area, which method comprises the steps of:
    (a) mechanically removing only said epithelium from said area, whereby within said area said Bowman's layer is the externally exposed anterior surface of said cornea; and
    (b) then directionally within said area impacting said exposed surface with tissue-ablating laser radiation to ablate said exposed anterior surface of said cornea with volumetric removal of corneal tissue to such penetration depth and profile as to characterize said exposed anterior surface of said cornea with said subsequent curvature.--.

Signed and Sealed this

Twenty-third Day of May, 1995

Attest:

BRUCE LEHMAN

Attesting Officer     Commissioner of Patents and Trademarks